(12) United States Patent
Stein et al.

(10) Patent No.: US 8,940,030 B1
(45) Date of Patent: Jan. 27, 2015

(54) SPINAL FIXATION SYSTEM AND RELATED METHODS

(75) Inventors: Christopher Stein, Fallbrook, CA (US);
Chad Grant, Escondido, CA (US);
Nathan Lovell, Oceanside, CA (US);
Ryan Donahoe, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 143 days.

(21) Appl. No.: 13/361,855

(22) Filed: Jan. 30, 2012

Related U.S. Application Data

(60) Provisional application No. 61/437,006, filed on Jan. 28, 2011.

(51) Int. Cl.
*A61B 17/80* (2006.01)

(52) U.S. Cl.
USPC .......................... 606/294; 606/295; 606/296

(58) Field of Classification Search
USPC ......................................... 606/289, 295, 296
See application file for complete search history.

(56) References Cited

U.S. PATENT DOCUMENTS

| 564,097 | A | 7/1896 | Nerud |
|---|---|---|---|
| 3,016,077 | A | 1/1962 | Yocum |
| 4,484,570 | A | 11/1984 | Sutter |
| 4,488,543 | A | 12/1984 | Tornier |
| 5,364,399 | A | 11/1994 | Lowery |
| 5,520,690 | A | 5/1996 | Errico |
| 5,531,554 | A | 7/1996 | Jeanson |
| 5,578,034 | A | 11/1996 | Estes |
| 5,843,082 | A | 12/1998 | Yuan |
| 5,931,838 | A | 8/1999 | Vito |
| 5,951,558 | A | 9/1999 | Fiz |
| 5,954,722 | A | 9/1999 | Bono |
| 5,979,907 | A | 11/1999 | Udagawa |
| 6,117,173 | A | 9/2000 | Taddia |
| 6,139,550 | A | 10/2000 | Michelson |
| 6,152,927 | A | 11/2000 | Farris |
| 6,193,721 | B1 | 2/2001 | Michelson |
| 6,224,602 | B1 | 5/2001 | Hayes |
| 6,235,033 | B1 | 5/2001 | Brace |
| 6,241,731 | B1 | 6/2001 | Fiz |
| 6,258,092 | B1 | 7/2001 | Dall |
| 6,261,291 | B1 | 7/2001 | Talaber |
| 6,306,139 | B1 | 10/2001 | Fuentes |
| 6,331,179 | B1 | 12/2001 | Freid |
| 6,361,537 | B1 | 3/2002 | Anderson |
| 6,413,259 | B1 | 7/2002 | Lyons |
| 6,558,423 | B1 | 5/2003 | Michelson |
| 6,602,255 | B1 | 8/2003 | Campbell |
| 6,602,257 | B1 | 8/2003 | Thramann |
| 6,613,053 | B1 | 9/2003 | Collins |
| 6,652,525 | B1 | 11/2003 | Assaker |

(Continued)

FOREIGN PATENT DOCUMENTS

| AU | 2012211502 | 8/2012 |
|---|---|---|
| CA | 2444232 | 8/1998 |

(Continued)

*Primary Examiner* — Andrew Yang
(74) *Attorney, Agent, or Firm* — Jonathan Spangler; Jennifer Russell

(57) ABSTRACT

The present invention relates generally to medical devices and methods for use in spinal surgery. In particular, the disclosed devices relate to a spinal fixation system and an intervertebral spinal implant assembly sized and dimensioned for the lumbar spine implantable via an anterior or anterolateral approach. The devices include an implant, bone screws, and an improved locking mechanism to prevent the back out of screws.

9 Claims, 6 Drawing Sheets

(56) References Cited

U.S. PATENT DOCUMENTS

| | | |
|---|---|---|
| 6,669,700 B1 | 12/2003 | Farris |
| 6,972,019 B2 | 12/2005 | Michelson |
| 7,001,389 B1 | 2/2006 | Navarro |
| 7,025,769 B1 | 4/2006 | Ferree |
| 7,094,239 B1 | 8/2006 | Michelson |
| D564,097 S | 3/2008 | Olerud |
| 7,766,911 B1 | 8/2010 | Navarro |
| 7,780,666 B1 | 8/2010 | Navarro |
| 7,785,327 B1 | 8/2010 | Navarro |
| 7,887,547 B2 | 2/2011 | Campbell |
| 8,328,856 B1 | 12/2012 | Donahoe |
| 2002/0004683 A1 | 1/2002 | Michelson |
| 2002/0045899 A1 | 4/2002 | Errico |
| 2002/0065517 A1 | 5/2002 | Paul |
| 2002/0095155 A1 | 7/2002 | Michelson |
| 2002/0099376 A1 | 7/2002 | Michelson |
| 2002/0099378 A1 | 7/2002 | Michelson |
| 2002/0103487 A1 | 8/2002 | Errico |
| 2002/0128655 A1 | 9/2002 | Michelson |
| 2002/0147450 A1 | 10/2002 | Lehuec |
| 2002/0151899 A1 | 10/2002 | Bailey |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0040749 A1 | 2/2003 | Grabowski |
| 2003/0060828 A1 | 3/2003 | Michelson |
| 2003/0078583 A1 | 4/2003 | Biedermann |
| 2003/0105462 A1 | 6/2003 | Haider |
| 2003/0171753 A1 | 9/2003 | Collins |
| 2003/0171754 A1 | 9/2003 | Del Medico |
| 2003/0187440 A1 | 10/2003 | Richelsoph |
| 2003/0187442 A1 | 10/2003 | Richelsoph |
| 2003/0191471 A1 | 10/2003 | Michelson |
| 2003/0191472 A1 | 10/2003 | Michelson |
| 2003/0199876 A1 | 10/2003 | Brace |
| 2003/0199983 A1 | 10/2003 | Michelson |
| 2003/0225409 A1 | 12/2003 | Freid |
| 2004/0015169 A1 | 1/2004 | Gause |
| 2004/0024464 A1 | 2/2004 | Errico |
| 2004/0030338 A1 | 2/2004 | Paul |
| 2004/0034352 A1 | 2/2004 | Needham |
| 2004/0039387 A1 | 2/2004 | Gause |
| 2004/0068318 A1 | 4/2004 | Coates |
| 2004/0068319 A1 | 4/2004 | Cordaro |
| 2004/0087951 A1 | 5/2004 | Khalili |
| 2004/0097934 A1 | 5/2004 | Farris |
| 2004/0122426 A1 | 6/2004 | Michelson |
| 2004/0127896 A1 | 7/2004 | Lombardo |
| 2004/0127897 A1 | 7/2004 | Freid |
| 2004/0127899 A1 | 7/2004 | Konieczynski |
| 2004/0127900 A1 | 7/2004 | Konieczynski |
| 2004/0127904 A1 | 7/2004 | Konieczynski |
| 2004/0153069 A1 | 8/2004 | Paul |
| 2004/0153070 A1 | 8/2004 | Barker |
| 2004/0193269 A1 | 9/2004 | Fraser |
| 2004/0199254 A1 | 10/2004 | Louis |
| 2004/0215195 A1 | 10/2004 | Shipp |
| 2004/0220566 A1 | 11/2004 | Bray |
| 2004/0220572 A1 | 11/2004 | Michelson |
| 2004/0236334 A1 | 11/2004 | Michelson |
| 2004/0236335 A1 | 11/2004 | Michelson |
| 2004/0260306 A1 | 12/2004 | Fallin |
| 2005/0015131 A1 | 1/2005 | Fourcault |
| 2005/0021032 A1 | 1/2005 | Koo |
| 2005/0027296 A1 | 2/2005 | Thramann |
| 2005/0033294 A1 | 2/2005 | Garden |
| 2005/0038436 A1 | 2/2005 | Michelson |
| 2005/0043736 A1 | 2/2005 | Mathieu |
| 2005/0049593 A1 | 3/2005 | Duong |
| 2005/0049595 A1 | 3/2005 | Suh |
| 2005/0071006 A1 | 3/2005 | Kirschman |
| 2005/0071008 A1 | 3/2005 | Kirschman |
| 2005/0075633 A1 | 4/2005 | Ross |
| 2005/0137597 A1 | 6/2005 | Butler |
| 2005/0143742 A1 | 6/2005 | Porcher |
| 2005/0149026 A1 | 7/2005 | Butler |
| 2005/0149027 A1 | 7/2005 | Campbell |
| 2005/0177236 A1 | 8/2005 | Mathieu |
| 2005/0187551 A1 | 8/2005 | Orbay |
| 2005/0187552 A1 | 8/2005 | Michelson |
| 2005/0192577 A1 | 9/2005 | Mosca |
| 2005/0192580 A1 | 9/2005 | Dalton |
| 2005/0228386 A1 | 10/2005 | Ziolo |
| 2005/0234455 A1 | 10/2005 | Binder |
| 2005/0251137 A1 | 11/2005 | Ball |
| 2005/0261689 A1 | 11/2005 | Lin |
| 2005/0261690 A1 | 11/2005 | Binder |
| 2005/0273105 A1 | 12/2005 | Konieczynski |
| 2005/0283152 A1 | 12/2005 | Lindemann |
| 2006/0009770 A1 | 1/2006 | Speirs |
| 2006/0079901 A1 | 4/2006 | Ryan |
| 2006/0085071 A1 | 4/2006 | Lechmann |
| 2006/0100626 A1 | 5/2006 | Rathbun |
| 2006/0122602 A1 | 6/2006 | Konieczynski |
| 2006/0122604 A1 | 6/2006 | Gorhan |
| 2006/0149253 A1 | 7/2006 | Doubler |
| 2006/0149255 A1 | 7/2006 | Doubler |
| 2006/0149256 A1 | 7/2006 | Wagner |
| 2006/0155285 A1 | 7/2006 | Anderson |
| 2006/0161157 A1 | 7/2006 | Mosca |
| 2006/0167456 A1 | 7/2006 | Johnston |
| 2006/0167457 A1 | 7/2006 | Suddaby |
| 2006/0189990 A1 | 8/2006 | Farris |
| 2006/0195089 A1 | 8/2006 | Lehuec |
| 2006/0195100 A1 | 8/2006 | Kirschman |
| 2006/0200146 A1 | 9/2006 | Doubler |
| 2006/0200147 A1 | 9/2006 | Ensign |
| 2006/0229620 A1 | 10/2006 | Rothman |
| 2006/0235403 A1 | 10/2006 | Blain |
| 2006/0235409 A1 | 10/2006 | Blain |
| 2006/0235411 A1 | 10/2006 | Blain |
| 2006/0235412 A1 | 10/2006 | Blain |
| 2006/0235518 A1 | 10/2006 | Blain |
| 2006/0235533 A1 | 10/2006 | Blain |
| 2006/0247639 A1 | 11/2006 | Anderson |
| 2006/0264936 A1 | 11/2006 | Partin |
| 2006/0293668 A1 | 12/2006 | May |
| 2006/0293669 A1 | 12/2006 | Lindemann |
| 2007/0043369 A1 | 2/2007 | Wallenstein |
| 2007/0083203 A1 | 4/2007 | Ribeiro |
| 2007/0106388 A1 | 5/2007 | Michelson |
| 2007/0118125 A1 | 5/2007 | Orbay |
| 2007/0123879 A1 | 5/2007 | Songer |
| 2007/0123884 A1 | 5/2007 | Abdou |
| 2007/0162019 A1 | 7/2007 | Burns |
| 2007/0225717 A1 | 9/2007 | Hawkes |
| 2007/0225718 A1 | 9/2007 | Ensign |
| 2007/0233110 A1 | 10/2007 | Muhanna |
| 2007/0233120 A1 | 10/2007 | Thramann |
| 2007/0288025 A1 | 12/2007 | Peukert |
| 2008/0015694 A1 | 1/2008 | Tribus |
| 2008/0021476 A1 | 1/2008 | Kirschman |
| 2008/0033438 A1 | 2/2008 | Frizzell |
| 2008/0033448 A1 | 2/2008 | Robinson |
| 2008/0091206 A1 | 4/2008 | Johnson |
| 2008/0097442 A1 | 4/2008 | Dixon |
| 2008/0097444 A1 | 4/2008 | Erickson |
| 2008/0114359 A1 | 5/2008 | Murner |
| 2008/0119933 A1 | 5/2008 | Aebi |
| 2008/0172095 A1 | 7/2008 | Salerni |
| 2008/0177307 A1 | 7/2008 | Moskowitz |
| 2008/0177330 A1 | 7/2008 | Ralph |
| 2008/0234750 A1 | 9/2008 | Woods |
| 2008/0243192 A1 | 10/2008 | Jacene |
| 2008/0249575 A1 | 10/2008 | Waugh |
| 2008/0249625 A1 | 10/2008 | Waugh |
| 2008/0269758 A1 | 10/2008 | Baynham |
| 2008/0269806 A1 | 10/2008 | Zhang |
| 2008/0287999 A1* | 11/2008 | Markworth .......... 606/280 |
| 2008/0288000 A1 | 11/2008 | Cawley |
| 2008/0288001 A1 | 11/2008 | Cawley |
| 2008/0300634 A1 | 12/2008 | Gray |
| 2008/0306550 A1 | 12/2008 | Matityahu |

(56) References Cited

U.S. PATENT DOCUMENTS

| | | |
|---|---|---|
| 2008/0306596 A1 | 12/2008 | Jones |
| 2008/0312699 A1 | 12/2008 | Johnson |
| 2009/0012571 A1 | 1/2009 | Perrow |
| 2009/0024170 A1 | 1/2009 | Kirschman |
| 2009/0030466 A1 | 1/2009 | Strauss |
| 2009/0030520 A1 | 1/2009 | Biedermann |
| 2009/0036933 A1 | 2/2009 | Dube |
| 2009/0054930 A1 | 2/2009 | Aflatoon |
| 2009/0062862 A1 | 3/2009 | Perrow |
| 2009/0062863 A1 | 3/2009 | Peppers |
| 2009/0080997 A1 | 3/2009 | Johnson |
| 2009/0088807 A1 | 4/2009 | Castaneda |
| 2009/0088808 A1 | 4/2009 | Lindemann |
| 2009/0105831 A1 | 4/2009 | Jones |
| 2009/0131988 A1 | 5/2009 | Bush |
| 2009/0149888 A1 | 6/2009 | Abdelgany |
| 2009/0182383 A1 | 7/2009 | Prybyla |
| 2009/0182430 A1 | 7/2009 | Tyber |
| 2009/0187218 A1 | 7/2009 | Schaffhausen |
| 2009/0192549 A1 | 7/2009 | Sanders |
| 2009/0192553 A1 | 7/2009 | Maguire |
| 2009/0192613 A1 | 7/2009 | Wing |
| 2009/0210011 A1 | 8/2009 | Den Hartog |
| 2009/0222049 A1 | 9/2009 | Frigg |
| 2009/0224023 A1 | 9/2009 | Moskowitz |
| 2009/0234393 A1 | 9/2009 | Sournac |
| 2009/0264934 A1 | 10/2009 | Youssef |
| 2009/0270926 A1 | 10/2009 | Hawkes |
| 2009/0270927 A1 | 10/2009 | Perrow |
| 2009/0287257 A1 | 11/2009 | Hagen |
| 2009/0306667 A1 | 12/2009 | Lee |
| 2009/0318978 A1 | 12/2009 | Podgorski |
| 2009/0326580 A1 | 12/2009 | Anderson |
| 2010/0004747 A1 | 1/2010 | Lin |
| 2010/0016901 A1 | 1/2010 | Robinson |
| 2010/0042159 A1 | 2/2010 | Butler |
| 2010/0042162 A1 | 2/2010 | Edie |
| 2010/0049256 A1 | 2/2010 | Jeon |
| 2010/0057128 A1 | 3/2010 | Bullard |
| 2010/0057206 A1 | 3/2010 | Duffield |
| 2010/0087871 A1 | 4/2010 | Loyola |
| 2010/0087925 A1 | 4/2010 | Kostuik |
| 2010/0106249 A1 | 4/2010 | Tyber |
| 2010/0121382 A1 | 5/2010 | Weiman |
| 2010/0121383 A1 | 5/2010 | Stanaford |
| 2010/0145459 A1 | 6/2010 | Mcdonough |
| 2010/0145460 A1 | 6/2010 | Mcdonough |
| 2010/0145463 A1 | 6/2010 | Michelson |
| 2010/0191240 A1 | 7/2010 | Prager |
| 2010/0191291 A1 | 7/2010 | Phan |
| 2010/0204737 A1 | 8/2010 | Bae |
| 2010/0204739 A1 | 8/2010 | Bae |
| 2010/0204796 A1 | 8/2010 | Bae |
| 2010/0211116 A1 | 8/2010 | Suh |
| 2010/0217393 A1 | 8/2010 | Theofilos |
| 2010/0222814 A1 | 9/2010 | Freid |
| 2010/0241174 A1 | 9/2010 | Robinson |
| 2010/0256686 A1 | 10/2010 | Fisher |
| 2010/0274294 A1 | 10/2010 | Biedermann |
| 2010/0274358 A1 | 10/2010 | Mueller |
| 2010/0286781 A1 | 11/2010 | Bullard |
| 2010/0292696 A1 | 11/2010 | Chantelot |
| 2010/0305704 A1 | 12/2010 | Messerli |
| 2010/0312346 A1 | 12/2010 | Kueenzi |
| 2011/0004253 A1 | 1/2011 | Fraser |
| 2011/0015745 A1 | 1/2011 | Bucci |
| 2011/0022096 A1 | 1/2011 | Cummins |
| 2011/0029024 A1 | 2/2011 | Crainich |
| 2011/0040382 A1 | 2/2011 | Muhanna |
| 2011/0054542 A1 | 3/2011 | Kevin |
| 2011/0054543 A1 | 3/2011 | Kevin |
| 2011/0054544 A1 | 3/2011 | Kevin |
| 2011/0071575 A1 | 3/2011 | Bhatnagar |
| 2011/0098747 A1 | 4/2011 | Donner |
| 2011/0106159 A1 | 5/2011 | Nazeck |
| 2011/0106171 A1 | 5/2011 | Kirschman |
| 2011/0125267 A1 | 5/2011 | Michelson |
| 2011/0137344 A1 | 6/2011 | Rathbun |
| 2011/0152944 A1 | 6/2011 | Campbell |
| 2011/0160860 A1 | 6/2011 | Johnston |
| 2011/0160866 A1 | 6/2011 | Laurence |
| 2011/0166656 A1 | 7/2011 | Thalgott |
| 2011/0166657 A1 | 7/2011 | Thalgott |
| 2011/0166658 A1 | 7/2011 | Garber |
| 2011/0172666 A1 | 7/2011 | Heilman |
| 2011/0172774 A1 | 7/2011 | Varela |
| 2011/0172780 A1 | 7/2011 | Scheland |
| 2011/0178551 A1 | 7/2011 | Eckhardt |
| 2011/0178599 A1 | 7/2011 | Brett |
| 2011/0184415 A1 | 7/2011 | Anderson |
| 2011/0190892 A1 | 8/2011 | Kirschman |
| 2011/0218628 A1 | 9/2011 | Ciupik |
| 2011/0230918 A1 | 9/2011 | Gorek |
| 2011/0230971 A1 | 9/2011 | Donner |
| 2011/0251689 A1 | 10/2011 | Seifert |
| 2011/0270322 A1 | 11/2011 | Olsen |
| 2011/0270323 A1 | 11/2011 | Olsen |
| 2011/0270326 A1 | 11/2011 | Black |
| 2011/0301713 A1 | 12/2011 | Theofilos |
| 2011/0301714 A1 | 12/2011 | Theofilos |
| 2011/0313421 A1 | 12/2011 | Sidebotham |
| 2011/0319893 A1* | 12/2011 | Stanaford et al. ............... 606/70 |
| 2011/0319943 A1 | 12/2011 | Donahoe |
| 2012/0016365 A1 | 1/2012 | Freid |
| 2012/0041494 A1 | 2/2012 | Cowan |
| 2012/0041558 A1 | 2/2012 | Robertson |
| 2012/0041559 A1 | 2/2012 | Melkent |
| 2012/0053638 A1 | 3/2012 | Rusch |
| 2012/0065688 A1 | 3/2012 | Nehls |
| 2012/0065734 A1 | 3/2012 | Barrett |
| 2012/0078310 A1 | 3/2012 | Bernstein |
| 2012/0078371 A1 | 3/2012 | Gamache |
| 2012/0078372 A1 | 3/2012 | Gamache |
| 2012/0078373 A1 | 3/2012 | Gamache |
| 2012/0095514 A1 | 4/2012 | Lombardo |
| 2012/0130495 A1 | 5/2012 | Duffield |
| 2012/0130496 A1 | 5/2012 | Duffield |
| 2012/0136392 A1 | 5/2012 | Keegan |
| 2012/0143336 A1 | 6/2012 | Aflatoon |
| 2012/0143341 A1 | 6/2012 | Zipnick |
| 2012/0158069 A1 | 6/2012 | Abrahams |
| 2012/0172987 A1 | 7/2012 | Phillips |
| 2012/0172989 A1 | 7/2012 | Mccarthy |
| 2012/0179207 A1 | 7/2012 | Mekhail |
| 2012/0179259 A1 | 7/2012 | Mcdonough |
| 2012/0197399 A1 | 8/2012 | Kirschman |
| 2012/0197401 A1 | 8/2012 | Duncan |
| 2012/0203348 A1 | 8/2012 | Michelson |
| 2012/0209331 A1 | 8/2012 | Michelson |
| 2012/0226319 A1 | 9/2012 | Armstrong |
| 2012/0226357 A1 | 9/2012 | Varela |
| 2012/0232663 A1 | 9/2012 | Zipnick |
| 2012/0245641 A1 | 9/2012 | Mekhail |
| 2012/0245690 A1 | 9/2012 | Cowan |
| 2012/0245693 A1 | 9/2012 | Gorek |
| 2012/0265259 A1 | 10/2012 | Laposta |
| 2012/0277867 A1 | 11/2012 | Kana |
| 2012/0277872 A1 | 11/2012 | Kana |
| 2012/0277873 A1 | 11/2012 | Kana |
| 2012/0290089 A1 | 11/2012 | Melamed |
| 2012/0303069 A1 | 11/2012 | Lin |
| 2012/0303126 A1 | 11/2012 | Kirschman |
| 2012/0316606 A1 | 12/2012 | Farin |
| 2012/0330417 A1 | 12/2012 | Zipnick |
| 2012/0330419 A1 | 12/2012 | Moskowitz |
| 2013/0023939 A1 | 1/2013 | Pischl |
| 2013/0046348 A1 | 2/2013 | Black |
| 2013/0053894 A1 | 2/2013 | Gamache |
| 2013/0053967 A1 | 2/2013 | Sournac |
| 2013/0060289 A1 | 3/2013 | Robinson |
| 2013/0060291 A1 | 3/2013 | Petersheim |
| 2013/0060336 A1 | 3/2013 | Hooper |
| 2013/0060337 A1 | 3/2013 | Petersheim |
| 2013/0066379 A1 | 3/2013 | Campbell |

(56) References Cited

U.S. PATENT DOCUMENTS

| | | |
|---|---|---|
| 2013/0073045 A1 | 3/2013 | Vestgaarden |
| 2013/0096688 A1 | 4/2013 | Michelson |
| 2013/0110242 A1 | 5/2013 | Kirwan |
| 2013/0110247 A1 | 5/2013 | Doran |
| 2013/0123925 A1 | 5/2013 | Patterson |
| 2013/0150969 A1 | 6/2013 | Zipnick |
| 2013/0172939 A1 | 7/2013 | Ziolo |
| 2013/0184766 A1 | 7/2013 | Black |
| 2013/0190825 A1 | 7/2013 | Perrow |
| 2013/0204372 A1 | 8/2013 | Mohar |
| 2013/0245688 A1 | 9/2013 | Biedermann |
| 2013/0338777 A1 | 12/2013 | Bagga |
| 2013/0345760 A1 | 12/2013 | Lombardo |
| 2013/0345814 A1 | 12/2013 | Walkenhorst |

FOREIGN PATENT DOCUMENTS

| | | |
|---|---|---|
| CA | 2523814 | 8/1998 |
| CA | 2533713 | 8/1998 |
| CN | 1366866 | 9/2002 |
| CN | 201216642 | 4/2009 |
| CN | 202477905 | 10/2012 |
| CN | 102860888 | 1/2013 |
| CN | 102973336 | 3/2013 |
| CN | 103099662 | 5/2013 |
| CN | 202960832 | 6/2013 |
| DE | 202008005076 | 9/2008 |
| DE | 202012006162 | 8/2012 |
| EP | 0903113 | 3/1999 |
| EP | 1690508 | 8/2006 |
| EP | 2457541 | 5/2012 |
| FR | 2790198 | 9/2000 |
| FR | 2874316 | 2/2006 |
| FR | 2973221 | 10/2012 |
| JP | 2013075120 | 4/2013 |
| KR | 20050032731 | 4/2005 |
| WO | WO-0024325 | 10/2000 |
| WO | WO-0064359 | 11/2000 |
| WO | WO-0078238 | 12/2000 |
| WO | WO-2004017837 | 3/2004 |
| WO | WO-2004112627 | 12/2004 |
| WO | WO-2005034796 | 4/2005 |
| WO | WO-2005053550 | 6/2005 |
| WO | WO-2006022644 | 3/2006 |
| WO | WO-2007037774 | 4/2007 |
| WO | WO-2007041638 | 4/2007 |
| WO | WO-2010028095 | 3/2010 |
| WO | WO-2011028236 | 3/2011 |
| WO | WO-2011057187 | 5/2011 |
| WO | WO-2011060073 | 5/2011 |
| WO | WO-2011092399 | 8/2011 |
| WO | WO-2012048920 | 4/2012 |
| WO | WO-2012094647 | 7/2012 |
| WO | WO-2012103254 | 8/2012 |
| WO | WO-2012115631 | 8/2012 |
| WO | WO-2012118846 | 9/2012 |
| WO | WO-2012141715 | 10/2012 |
| WO | WO-2012148499 | 11/2012 |
| WO | WO-2012148500 | 11/2012 |
| WO | WO-2013008111 | 1/2013 |
| WO | WO-2013014590 | 1/2013 |
| WO | WO-2013032805 | 3/2013 |
| WO | WO-2013048000 | 4/2013 |
| WO | WO-2013072582 | 5/2013 |
| WO | WO-2013116952 | 8/2013 |
| WO | WO-2013167895 | 11/2013 |

* cited by examiner

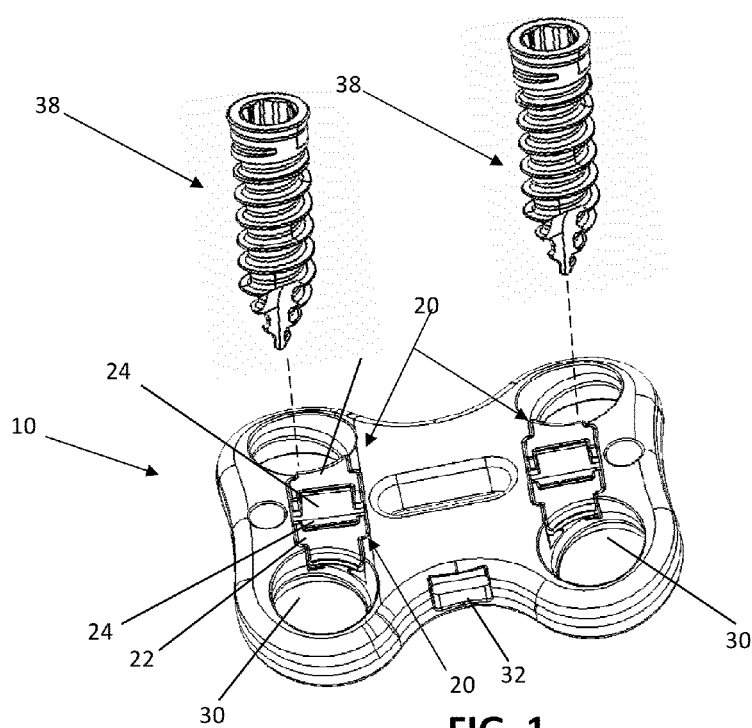
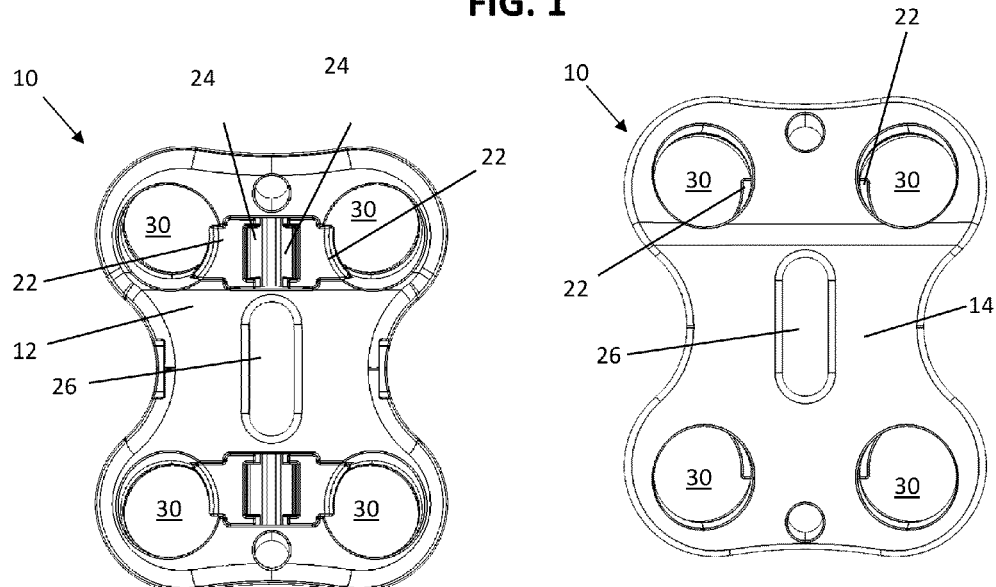
FIG. 1
FIG. 2
FIG. 3

SPINAL FIXATION SYSTEM AND RELATED METHODS

CROSS REFERENCE TO RELATED APPLICATIONS

This application is a non-provisional patent application claiming the benefit of priority from U.S. Provisional Patent Application Ser. No. 61/437,006, filed on Jan. 28, 2011, the entire contents of which are hereby expressly incorporated by reference into this disclosure as if set forth in its entirety herein.

FIELD

The present invention relates generally to spinal surgery and, more particularly, to devices for spinal fixation and spinal fusion having an improved mechanism to prevent the back out of screws.

BACKGROUND

Currently there are nearly 500,000 spine lumbar and cervical fusion procedures are performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Anterior lumbar interbody fusion (ALIF) procedures provide unparalleled access to a desired spinal target site. The ALIF technique involves approaching the spine through the abdomen and exposing the front of the spine, as opposed to the side or the back. Approaching the spine this way generally allows for greater exposure and a more complete excision of the damaged disc. Introducing the intervertebral implant serves to restore the height between adjacent vertebrae ("disc height"), which reduces if not eliminates neural impingement commonly associated with a damaged or diseased disc.

SUMMARY

According to one embodiment, a surgical fixation system is described including a plate dimensioned to span at least two bony segments, a plurality of apertures dimensioned to receive anchor elements, a plurality of anchor elements and plurality anti-backout elements disposed adjacent to each of the apertures dimensioned to receive anchor elements.

According to an exemplary embodiment, the anti-backout element comprises a biasing member and a locking slide. The biasing member is elastically deformable. In a first position, the biasing member urges the locking slide in a first direction in which at least a portion of the locking slide enters the aperture in the plate. Upon insertion of an anchor element, the anchor element may force the locking slide to move in a second direction opposite the first direction, deforming the biasing member and moving the biasing member to a second position such that the locking slide does not reside in the aperture of the plate. Once the anchor element is fully inserted through the plate and passed the locking slide, the biasing member urges the locking slide in the first direction into the aperture such that at least a portion of the locking slide covers the proximal end of the anchor element preventing the anchor element from backing out of the plate.

According to another embodiment, a spinal fusion implant assembly is described. The spinal fusion implant assembly includes a plate coupled to a U-shaped body, a plurality of apertures in the plate dimensioned to receive anchor elements, a plurality of anchor elements and a plurality of anti-backout elements.

The anti-backout element includes a biasing member and locking slide and operates in the same way as described above for the surgical fixation system.

According to an exemplary aspect, the plate and the U-shaped body of the spinal fusion implant assembly are constructed of different materials. When fully assembled, the spinal fusion implant assembly is dimensioned to be contained entirely within an intervertebral disc space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 1 is a perspective view of a spinal fixation system, according to an exemplary embodiment;

FIG. 2 is a top view of the spinal fixation plate of FIG. 1;

FIG. 3 is a bottom view of the spinal fixation plate of FIG. 1;

DESCRIPTION OF THE PREFERRED EMBODIMENT

Figure 4:
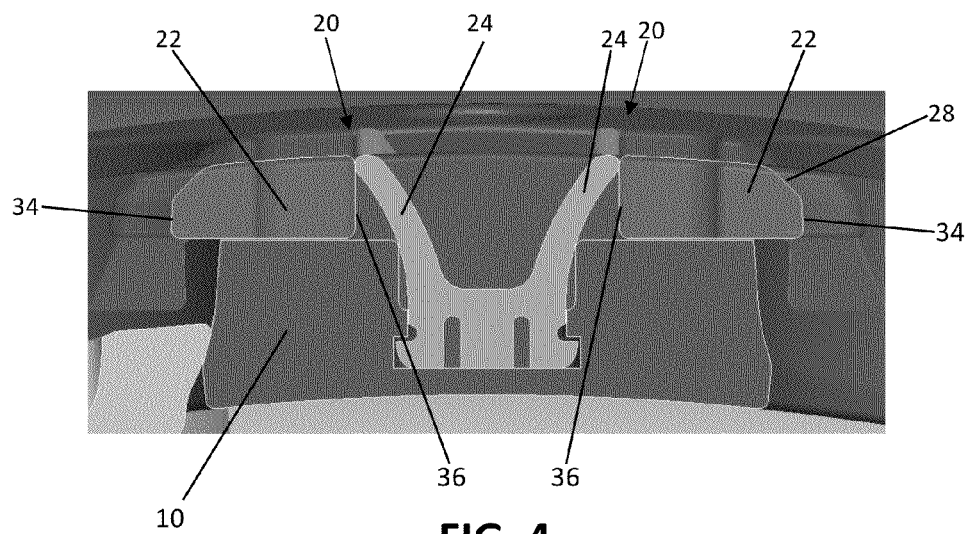
FIG. 4 is a cross-section of the width of the spinal fixation plate of FIG. 1.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal implants disclosed herein boast a variety of inventive features and components that warrant patent protection, both individually and in combination.

FIGS. 1-6 illustrate an example of a surgical fixation system, according to an exemplary embodiment. The surgical fixation system comprises a surgical fixation plate 10, a plurality of screws 38 (only two of four shown), and a plurality of anti-backout elements 20. As will be explained in greater detail below, the surgical fixation system may be used to provide temporary or permanent fixation along an orthopedic target site, including but not limited to adjacent vertebral levels within the spine (e.g. cervical spine during anterior fusion surgery, lumbar spine for anterior fusion surgery, etc. . . . ). To do so, the plate 10 is first positioned over the target site such that the screws and anti-backout elements 20 may thereafter be employed to couple the plate 10 to the target site. According to one aspect of the present invention, the screws 38 are prevented from backing out of the target site after placement through the use of the anti-backout elements 20 installed within the plate 10.

The surgical fixation plate 10 includes a first surface 12, a second surface 14, and a plurality of bone screw apertures 30 extending between the first and second surfaces 12, 14. Each bone screw aperture 30 has a corresponding anti-backout element 20 for preventing back-out of only one screw 38. The anti-backout element 20 resides in a recess 40 in first surface 12 of the plate 10 adjacent to the bone screw aperture 30.

The plate 10 may be provided having any number of different peripheral profiles, including but not limited to the generally rectangular peripheral profile set forth by way of example in the figures. The plate 10 may also be provided with or without a viewing aperture 40 formed between the first and second surfaces 12, 14 and positioned generally in the central portion of plate 10. The viewing aperture 40 functions to provide the ability to see or visualize the spinal target site after the plate 10 has been secured to the patient's vertebrae. It will be appreciated that the viewing aperture 40 may be provided in any number of suitable shapes or configurations without departing from the scope of the invention. Insertion tool recesses 32 may be provided on the lateral sides of the plate 10 for receiving at least a portion of an insertion instrument. By way of example only, the plate 10 shown in FIGS. 1-6 includes a pair of insertion tool recesses 32, with one located at each side of the plate 10.

FIGS. 1-6 illustrate a plate 10 having an anti-backout element 20 according to an exemplary embodiment. The anti-backout element 20 includes a locking slide 22 and a biasing member 24. The biasing member 24 is coupled to the plate 10 medial to the locking slide 22, and urges the locking slide 22 toward the screw aperture 30. The biasing member 24 is elastically deformable, such that when a bone screw 38 is inserted into the screw aperture 30, the head of the screw will urge the locking slide 22 away from the screw aperture 30 against the biasing member 24, thereby deforming the biasing member 24. Upon passage of the screw head past the locking slide 22, into the screw aperture 30, the biasing member 24 will urge the locking slide 22 back toward the screw aperture 30. At least a portion of the locking slide 22 will project into the screw aperture 30 (as best shown in FIG. 3), and over the proximal edge of the screw head, thereby preventing the screw from backing out of the screw aperture 30 of the plate 10 after insertion.

Figure 5:
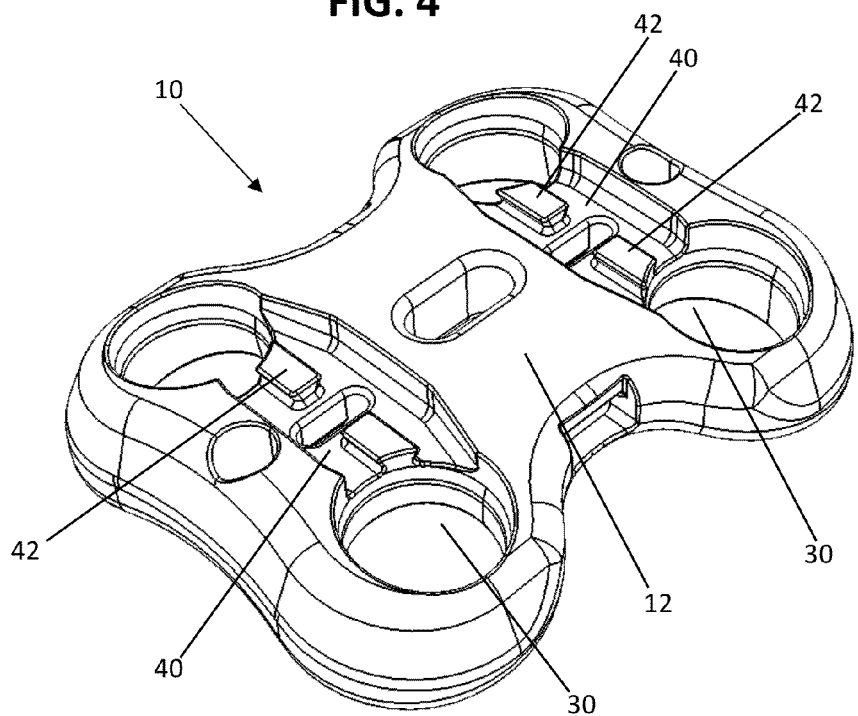
FIG. 5 is a perspective view of the spinal fixation plate of FIG. 1, without the anti-back-out mechanism.
Figure 6:
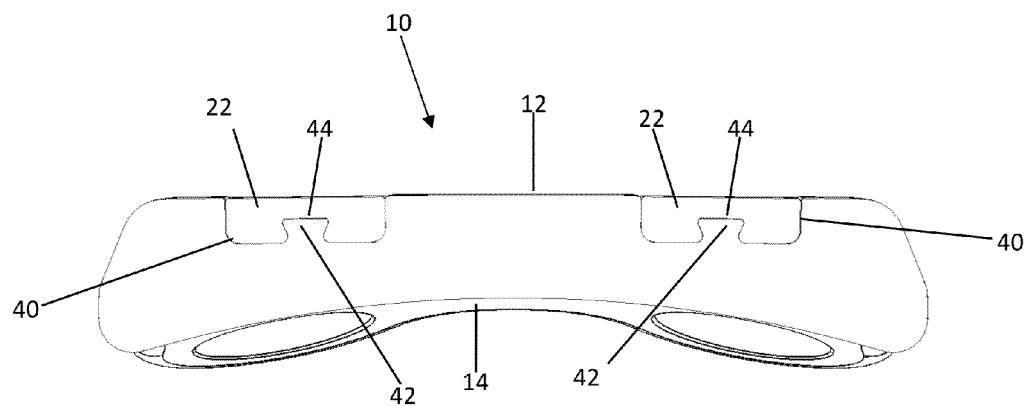
FIG. 6 is a cross-section along the longitudinal axis of the spinal fixation plate of FIG. 1.

The locking slide 22 has a medial face 36 for engaging the biasing member 24 and a lateral face 34 for engaging the head of a bone screw 38. According to the exemplary embodiment shown in FIGS. 1-6, the lateral face 34 that engages the head of a bone screw has a chamfered surface 28, such that during insertion of a bone screw 38 into a bone screw aperture 30 of the plate 10, when the head of the bone screw contacts the chamfered surface 28 of the locking slide 22, the medial surface 36 of the locking slide 22 will be urged against the biasing member 24 as discussed above. The locking slides may engage with the spinal fixation plate 10 within a recess 40 in the spinal fixation plate 10, wherein said recess 40 is located medially to a pair of screw apertures 30 (as best shown in FIG. 5). According to an exemplary embodiment, the locking slides 22 have a recess 44 that corresponds to a track 42 in the recess 40 in superior surface 12 of the plate 10. The track 42 engages the locking slide 22 via the recess 44 in the locking slide 22 and maintains the locking slide 22 within the plate 10. As such, the locking slide 22 is capable of sliding in a first direction toward its corresponding screw aperture 30 and in second direction, opposite the first direction, away from a corresponding screw aperture 30 and toward the biasing member 24.

Figure 7:
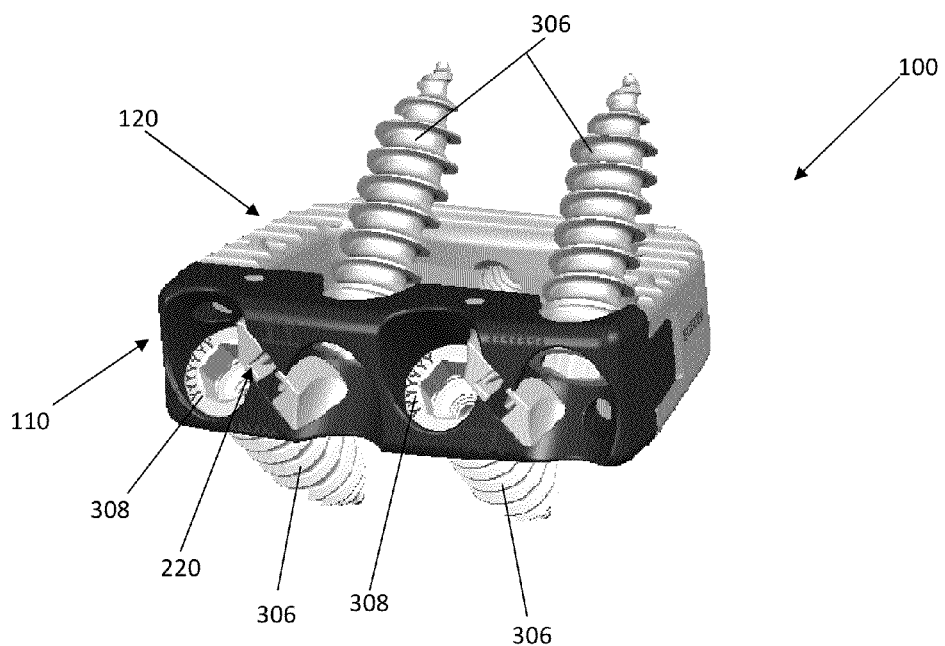
FIG. 7 is a perspective view of a spinal fusion implant assembly according to an exemplary embodiment.
Figure 8:
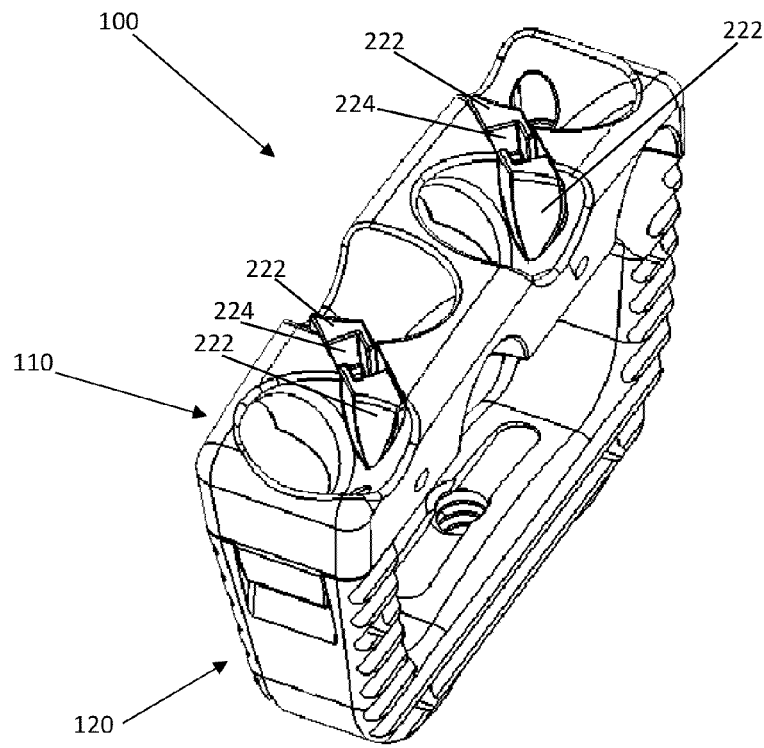
FIG. 8 is a perspective view of the spinal fusion implant assembly of FIG. 7.
Figure 12:
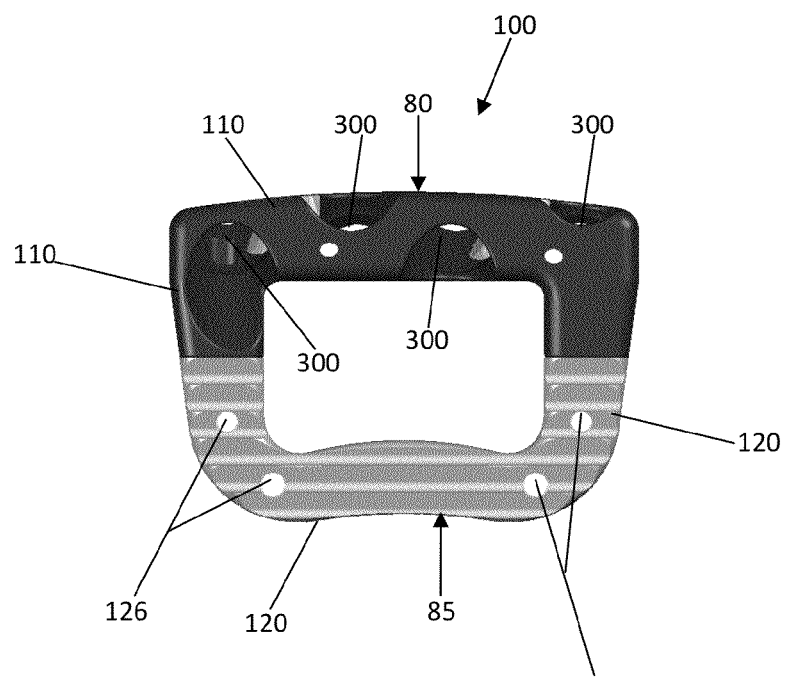
FIG. 12 is a top view of the spinal fusion implant assembly of FIG. 10.
Figure 13:
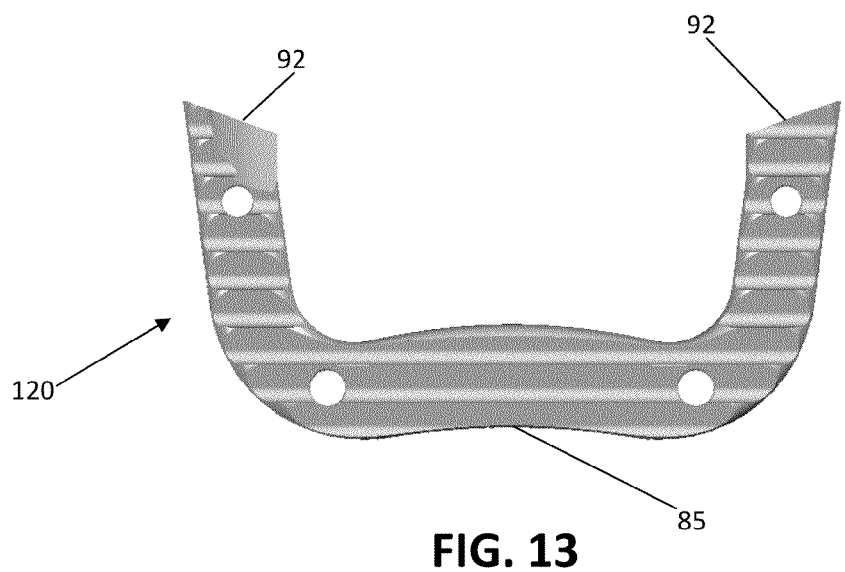
FIG. 13 is a front view of an alternative embodiment of the body of the implant assembly of FIGS. 7-12.

FIGS. 7-8 illustrate a spinal fusion implant assembly 100 according to an exemplary embodiment. The spinal fusion implant assembly 100 is a two-piece assembly including a plate 110 having locking elements 220, a plurality of bone screws 306 and a generally U-shaped body 120. The assembled two-piece implant 100 is dimensioned to be contained entirely within the intervertebral space when implanted. According to the exemplary embodiments, the plate 110 and body 120 are constructed of different materials. For example, the plate 110 may be constructed of any biocompatible metal, such as titanium. The body 120 may be constructed of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. According to an exemplary embodiment shown if FIG. 12, the arms of the U-shaped body may have chamfered surfaces where the body 120 engages the plate.

The spinal fusion implant assembly 100 includes a top surface 90, a bottom surface 95, two lateral sides, an anterior side 80, and a posterior side 85 (each defined relative to the regions of the target disc space when implanted). According to a preferred method of implantation the spinal fusion implant 100 may be implanted from an anterior approach such that anterior side 80 is the trailing side and posterior side 85 is the leading side during insertion. The plate 110 defines the anterior side 80 of the implant and includes a plurality of bone screw apertures 302, 304 each for receiving a bone screw therethrough. According to the exemplary embodiments, the screw apertures 302, 304 are positioned such that there is a lateral upper screw hole, a medial upper screw aperture, a lateral lower screw aperture, and a medial lower screw aperture.

The upper screw apertures 302 pass through the plate 110 at an angle such that when the bone screws 306 are inserted into the upper screw apertures 302, they extend from the plate 110 at an angle and penetrate into the vertebral body inferior to the implant assembly 100. By way of example only, the upper screw apertures 302 may be angled such that the bone screws penetrate into the vertebral body at an angle between 35 and 55 degrees, and preferably 45 degrees. Lower screw apertures 304 also pass through the plate 110 at an angle, but in the opposite direction of the upper screw apertures 302. Thus, when the bone screw 306 is inserted into the lower screw apertures 304, it extends from the plate 110 at an angle and penetrates the vertebral body superior to the implant assembly 100. By way of example, the lower screw apertures 304 may be angled such that the lower bone screws 306 penetrate into the vertebral body at an angle between 35 and 55 degrees, and preferably 45 degrees. The screw apertures 302, 304 may also be angled such that the distal end of the bone screws 306 converge towards each other. By way of example, the screw apertures 302, 304 may be oriented such that the bone screws 306 are angled medially between 5 and 15 degrees.

According to the exemplary embodiment illustrated in FIGS. 7-8, the plate 110 further includes an anti-backout element 220 that corresponds to each individual screw aperture 300. The anti-backout element 220 includes a locking slide 222 and a biasing member 224. The anti-backout element 220 functions in a way that is similar to the anti-backout element 20 described with respect to the spinal fixation plate 10 discussed above. A pair of locking elements 220 resides in a recess in the anterior surface of the plate 110 between a pair of screw apertures 300. The biasing member 224 is elastically deformable, such that when a bone screw 306 is inserted into the screw aperture 300, the head 308 of the screw will urge the locking slide 222 away from the screw aperture 300 against the biasing member 224, thereby deforming the biasing member 224. Upon passage of the screw head 308 past the locking slide 222, into the screw aperture 30, the biasing member 224 will urge the locking slide 222 back toward the screw aperture 300. At least a portion of the locking slide 222 will project into the screw aperture 300, and over proximal end of the screw head 308, thereby preventing the screw 306 from backing out of the screw aperture 300 of the plate 110 after insertion.

According to one embodiment, the body 120 includes at least one radiopaque marker 126. Further, the body 120 may also include anti-migration elements. Anti-migration features are designed to increase the friction between the spinal fusion implant assembly 100 and the adjacent contacting surfaces of the vertebral bodies so as to further prohibit migration of the spinal fusion implant 100 after placement and during the propagation of natural bony fusion. Such anti-migration features may include ridges (or teeth) provided along at least a portion of the top surface 90 and/or bottom surface 95.

Figure 9:
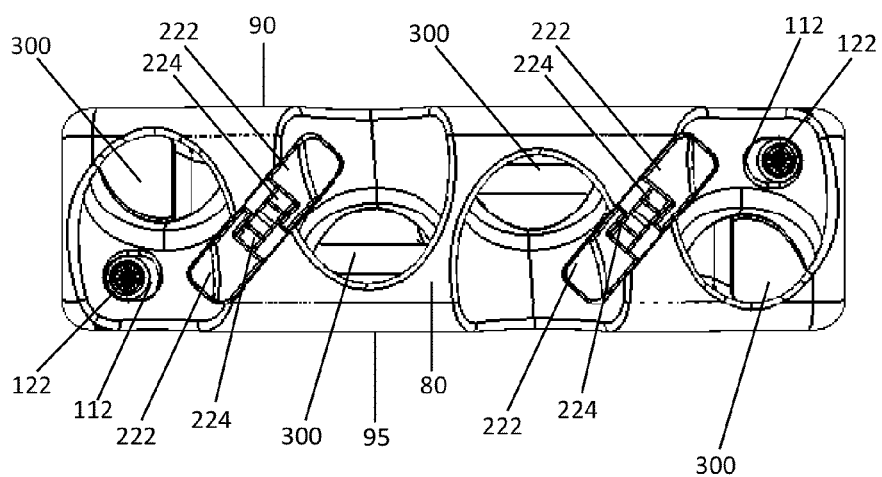
FIG. 9 is a front view of the spinal fusion implant assembly of FIG. 7.
Figure 10:
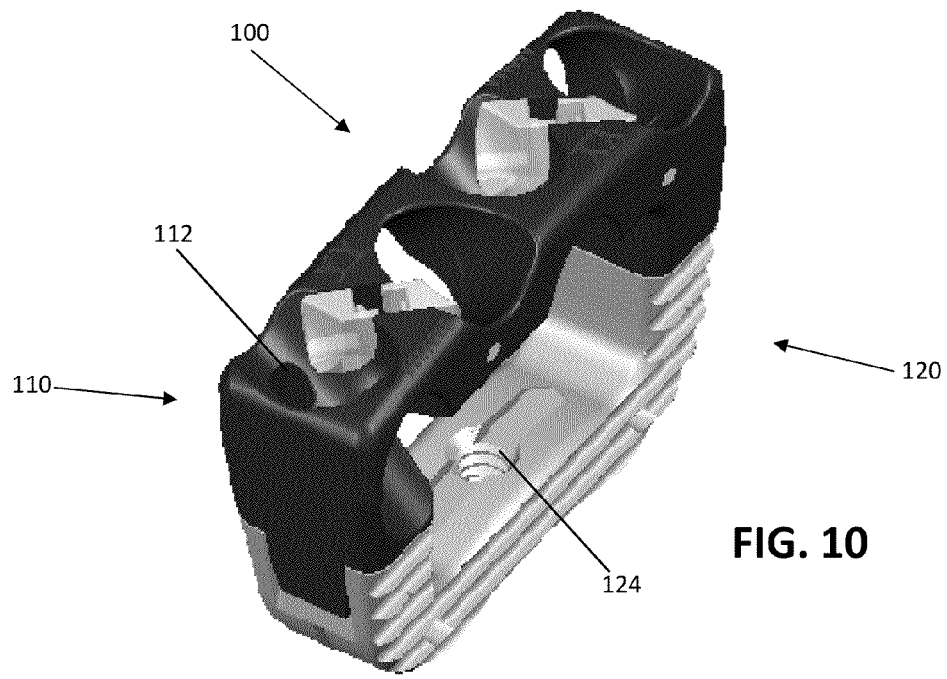
FIG. 10 is a perspective view of the spinal fusion implant assembly according to an alternate embodiment.
Figure 11:
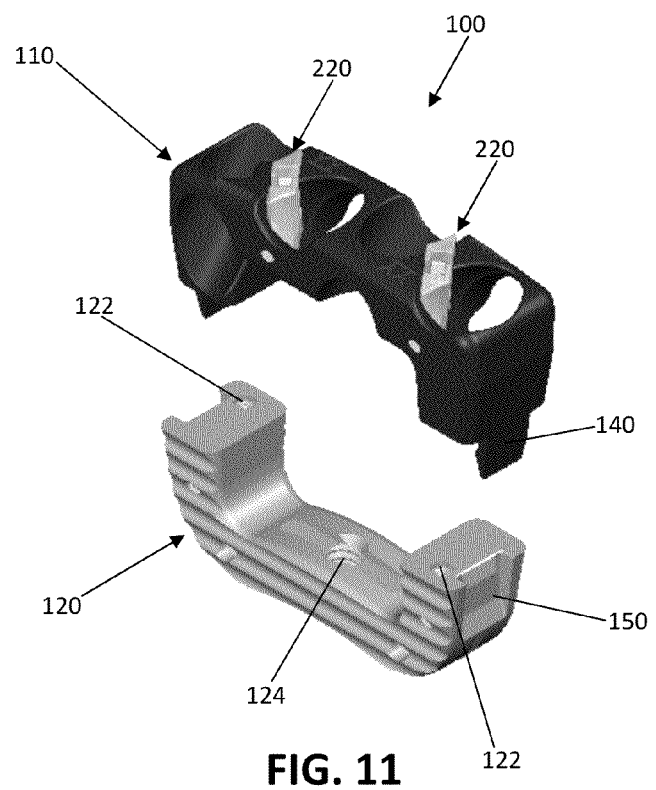
FIG. 11 is an exploded view of the spinal fusion implant assembly of FIG. 10.

FIGS. 9-11 illustrate an alternative embodiment of the spinal fusion implant assembly 100. This embodiment includes all of the same features as the exemplary embodiment of FIGS. 7-8. According to this embodiment, the plate 110 is generally U-shaped and the body 120 is generally U-shaped. The screw apertures 300 extend through the plate 110 from the anterior surface 80 through the top surface 90 (for lower screw apertures) of the plate 110 or the bottom surface 95 (for upper screw apertures) of the plate 110.

With regard to the embodiment shown in FIGS. 7-11, it is contemplated that the spinal fusion implant assembly 100 can be assembled prior to insertion into the intervertebral space and implanted as a single complete implant, or the implant assembly 100 can be assembled within the intervertebral disc space in a multi-step process including inserting the body 120 into the intervertebral space, packing the body 120 and/or disc space adjacent the body 120 with bone growth enhancing material, then inserting the plate 110 and coupling the plate 110 to the body 120, thereby enclosing bone growth material in the interior space of the implant assembly 100. Both methods of implantation are preferably achieved through a standard anterior approach. In order to facilitate assembly of the implant 100 within the intervertebral space, the body 120 includes an insertion tool aperture 124 to enable the body 120 of the assembly to be implanted in the intervertebral space before the plate 110.

According to the embodiments shown in FIGS. 7-11, the body further includes apertures 122 dimensioned to receive a guide element, such as a pin or wire (not shown). By way of example only, the guide element apertures 122 may be threaded to receive a guide element with a threaded distal end. Accordingly, the plate 110 also includes apertures 112 dimensioned to allow passage of a guide element therethough. The guide apertures 122 in the body align with the guide apertures 112 in the plate, such that after the body 120 is implanted in the intervertebral space with guide elements attached, the plate 110 can be inserted to align with the body 120. The plate 110 further includes engagement features 140 that correspond to engagement features 150 on the body to facilitate coupling of the plate 110 to the body 120 upon insertion of the plate 110 into the intervertebral space. Once the plate 110 is coupled to the body 120 within the disc space, the guide elements may be removed from the implant assembly 100.

The spinal fusion implant assembly 100 may be used to provide temporary or permanent fixation along an orthopedic target site. Once deposited in the intervertebral disc space, the spinal implant assembly 100 effects spinal fusion over time as the natural healing process integrates and binds the implant 100 within the intervertebral space by allowing a bony bridge to form through the implant 100 and between the adjacent vertebral bodies. Top surface 90 and opposed bottom surface 90 are both adapted for contact with the upper and lower vertebra adjacent the disc space. Bone screws may be introduced through the screw apertures 300 and into the adjacent vertebral bodies to fix the implant assembly 100 in the desired position within the disc space.

According to an additional embodiment, the top and bottom surfaces 90, 95 may be angled between the anterior side 80 and posterior side 85. In lumbar and cervical applications, the posterior side 85 will preferably be shorter in height than the anterior side 80 such that the implant 100 tapers down from anterior side 80 to posterior side 85. For example, the posterior-to-anterior angle of the tapered top and bottom surfaces 80, 85 may range from 5° and 15° relative to a horizontal axis, and preferably 8° to 12°. In this manner, the implant 100 helps maintain the adjacent vertebral bodies in lordosis, which is the natural curvature found in the lumbar and cervical regions of the spine. The top and bottom surfaces 80, 85 may be configured in any number of suitable shapes to better match the natural contours of the vertebral end plates, such as, for example, concave, convex, or a combination of concave and convex.

Fusion may be facilitated or augmented by introducing or positioning various osteoinductive materials within cavity between the plate 110 and the body 120 and/or adjacent to the spinal fusion implant assembly 100 within the intervertebral space. Such osteoinductive materials may be introduced before, during, or after insertion of the exemplary spinal fusion implant assembly 100, and may include (but are not necessarily limited to) autologous bone harvested from the patient receiving the spinal fusion implant assembly 100, bone allograft, bone xenograft, any number of non-bone implants (e.g. ceramic, metallic, polymer), bone morphogenic protein, and bio-resorbable compositions, including but not limited to, any of a variety of poly (D, L-lactice-co-glycolide) based polymers.

What is claimed is:

1. A surgical fixation system for fixing a first bony segment relative to a second bony segment, comprising:
    a bone plate sized to span at least two adjacent bone segments, said bone plate including a first aperture configured to receive an anchor element, said first aperture positioned relative to said first bony segment, and a second aperture configured to receive an anchor element, said second aperture positioned relative to said second bony segment;
    a plurality of anchor elements configured to anchor said bone plate to said first and second bony segments, each of said anchor elements dimensioned to be received through one of said first and second apertures; and a plurality of anti-backout elements disposed adjacent to each of said first and second apertures, said anti-backout elements configured to allow passage of at least a portion of said anchor element therethough in one direction while resisting passage of at least a portion of said anchor element therethrough in an opposite direction;

wherein said plurality of anti-backout elements comprise a locking slide and a biasing member, wherein said biasing member is physically distinct from said locking slide and elastically deformable from a first position urging at least a portion of said locking slide in a first direction into said aperture to a second position wherein said locking slide urges said biasing member in a direction opposite said first direction.

2. The surgical fixation system of claim 1, wherein said anchor elements are bone screws.

3. The surgical fixation system of claim 1, wherein said locking slide has a lateral side and a medial side.

4. The surgical fixation system of claim 1, wherein said lateral side includes a chamfered surface.

5. The surgical fixation system of claim 1, wherein said plate has an upper surface and a lower surface, wherein said upper surface includes a recess between said first and second apertures.

6. The surgical fixation system of claim 5, wherein said recess in said upper surface of said plate includes a track element therein.

7. The surgical fixation system of claim 6, wherein said locking slide includes a recess that corresponds to the shape of the track element in said recess in said upper surface of said plate, and wherein said locking slide is mated to the plate via the track element.

8. The surgical fixation system of claim 1, further comprising third and fourth apertures configured to receive an anchor element, said third aperture positioned adjacent said first aperture and relative to said first bony segment, said fourth aperture positioned adjacent said second aperture and relative to said second bony segment.

9. A method of performing spinal fusion surgery, comprising:

positioning a bone plate to span at least two adjacent bony segments, said bone plate including a first aperture configured to receive an anchor element and positioned relative to said first bony segment, a second aperture configured to receive an anchor element and positioned relative to said second bony segment, and a plurality of anti-backout elements disposed adjacent each of said first and second apertures, said anti-backout elements configured to allow passage of at least a portion of said anchor element therethrough in one direction while resisting passage of at least a portion of said anchor element therethrough in an opposite direction;

inserting an anchor element through each of said first and second apertures such that said anti-backout element covers at least a portion of said anchor element;

wherein said plurality of anti-backout elements comprise a biasing member and a locking slide, wherein said biasing member is physically distinct from the locking slide and elastically deformable from a first position urging at least a portion of said locking slide in a first direction into said aperture to a second position wherein said locking slide urges said biasing member in a direction opposite said first direction.

* * * * *